(12) United States Patent
O'Donnell, Jr.

(10) Patent No.: US 6,569,174 B1
(45) Date of Patent: May 27, 2003

(54) APPARATUS FOR LAMELLAR KERATOPLASTY

(76) Inventor: Francis E. O'Donnell, Jr., 709 The Hamptons La., Town & Country, MO (US) 63017

( * ) Notice: Subject to any disclaimer, the term of this patent is extended or adjusted under 35 U.S.C. 154(b) by 372 days.

(21) Appl. No.: 09/715,443

(22) Filed: Nov. 20, 2000

Related U.S. Application Data

(63) Continuation of application No. 09/300,048, filed on Apr. 27, 1999, now Pat. No. 6,197,038, which is a continuation-in-part of application No. 09/188,160, filed on Nov. 7, 1998, now abandoned.
(60) Provisional application No. 60/065,757, filed on Nov. 17, 1997.

(51) Int. Cl.[7] ............................................. A61B 17/32
(52) U.S. Cl. ..................................................... 606/166
(58) Field of Search ................................ 606/166, 167, 606/161, 107, 172

(56) References Cited

U.S. PATENT DOCUMENTS

| | | | |
|---|---|---|---|
| 4,662,370 A | 5/1987 | Hoffmann et al. | |
| 4,750,491 A * | 6/1988 | Kaufman et al. | 606/166 |
| 4,840,175 A | 6/1989 | Peyman | |
| 4,903,695 A | 2/1990 | Warner et al. | |
| 5,556,406 A | 9/1996 | Gordon et al. | |
| 5,586,980 A | 12/1996 | Kremer et al. | |
| 5,643,299 A | 7/1997 | Bair | |
| 5,989,272 A | 11/1999 | Barron et al. | |
| 6,296,649 B1 * | 10/2001 | Hellenkamp | 606/166 |

\* cited by examiner

*Primary Examiner*—Kevin T. Truong
(74) *Attorney, Agent, or Firm*—Paul M. Denk

(57) ABSTRACT

A microkeratome for improved corneal flap production for corneal surgery. The microkeratome, having a first aperture and a cutting blade, includes a second aperture located just below the plane of the cutting blade and through which a corneal plug protrudes in preparation for the lamellar cut of the microkeratome to create a uniformly thick lamellar flap of predetermined diameter and depth. The second aperture can include a second cutting blade. The microkeratome also includes a transparent applanation plate positioned at a predetermined distance above the plane of the cutting blade and an adjustable stop to prevent complete transection of the corneal flap.

13 Claims, 2 Drawing Sheets

APPARATUS FOR LAMELLAR KERATOPLASTY

CROSS-REFERENCE TO RELATED APPLICATIONS

This application is designated as a continuation of the applications Ser. No. 09/300,048, filed Apr. 27, 1999 now U.S. Pat. No. 6,197,038, which is a continuation-in-part of application Ser. No. 09/188,160, filed Nov. 7, 1998, now abandoned which claims priority to provisional application Serial No. 60/065,757, filed Nov. 17, 1997.

BACKGROUND OF THE INVENTION

This invention relates generally to the field of refractive corneal surgery and, in particular, to the use of a refractive laser in conjunction with an automated lamellar keratoplasty, so-called LASIK (laser-in-situ keratoplasty). The present invention teaches a novel apparatus for improving the creation of the lamellar corneal flap.

LASIK (laser-in-situ keratoplasty) is a refractive laser procedure used to correct refractive errors such as myopia, hyperopia, and astigmatism. Aspects of the procedure are disclosed and claimed in U.S. Pat. No. 4,840,175, to Peyman et al and U.S. Pat. No. 4,903,695, to Warner et al. In general the refractive procedure requires the creation of a lamellar corneal flap. A variety of mechanical cutting devices have been described to create the lamellar flap. These devices, generally known as "microkeratomes", differ principally in how they drive the blade (e.g. gears vs. cable) and how they flatten (applanate) the cornea during the lamellar cut. For example, U.S. Pat. No. 5,586,980, to Kremer et al discloses a microkeratome device.

The prior art microkeratome devices all share in common the creation of flaps of variable depth and size, depending somewhat upon corneal curvature. That is to say, "steep" corneas (e.g. central keratometry greater than 46 diopters) produce flaps of different size and thickness than do "flat" corneas (e.g. central keratometry less than 41 diopters). This variation occurs because the prior art devices all require an applanation of the cornea through a suction ring during the keratectomy. In the case of an extremely flat cornea, for example, the likelihood of an amputated flap (corneal cap) is very high. Variations in flap diameters compromise the laser correction by limiting the diameter of the ablation, which in turn affects centration and the degree of maximum correction and also may result in side effects, such as halos and ghosting.

Moreover, all these prior art devices use high suction pressure (elevates intraocular pressure to 90 mm Hg or more) to firm up the globe during the keratectomy. Loss of suction during the keratectomy can result in complications such as irregularly thick flap, lacerated flap, amputated flap, and aborted flap creation. Generally speaking, if the suction break occurs before completion of the keratectomy and it is detected by the surgeon, the case is aborted. The high intraocular pressure (often 90 mm Hg or more) created by a suction apparatus of the prior art can have well-recognized, serious complications such as intraocular vascular occlusion, macular hemorrhage, and retinal detachments.

Prior art lamellar keratectomy microkeratomes also share another common limitation, i.e., they all create a dome-shaped flap. The central thickness is generally desired to be 150–200 microns in order to provide adequate peripheral thickness. This flap contour is disadvantageous because it can mask the underlying stromal contour created by the laser ablations. In a myopic correction, for example, the laser creates a central concavity in the stromal bed, but the flap has a central convexity because of its dome shape.

Furthermore, the thin flap edges created by prior art devices are prone to melt. The flap edges are on the surface or the cornea, resulting in a greater likelihood that the flap will be distorted, displaced, or torn free by eyelid blinking or minor trauma such as rubbing the eyes. Prior art procedures rely upon hydrostatic pressure to seal the flap to the surface of the cornea.

Besides mechanical cutting microkeratomes which use oscillating metal or gem blades, other cutting modalities have been introduced such as pressured water jets, as provided in U.S. Pat. No. 5,643,299 to Blair, or lasers such as erbium:YAG. Nevertheless, these prior art techniques and devices share the aforementioned limitations of the mechanical cutting microkeratomes.

In my co-pending application Ser. No. 09/188,160, I provide an apparatus and method to eliminate the aforementioned limitations of the prior art. As such, that device provides an optionally thinner, but uniformly thick corneal flap of precisely determined diameter, regardless of corneal curvature. Furthermore, that device more reliably reproduces the curvature created by the laser, eliminates the risk of flap amputation (free cap), eliminates the risk of flap distortion, displacement, or tearing, and reduces the risk of epithelial ingrowth and eliminates the risk of complications associated with high suction pressure, such as intraocular vascular occlusion. However, the present invention discloses an improvement over that device and provides a novel apparatus for the microkeratome device used in creating a lamellar corneal flap and is intended to be used so as improve the method of performing the procedure disclosed in co-pending application Ser. No. 09/188,160.

SUMMARY OF THE INVENTION

It is among the various objects of the present invention to provide an apparatus to create a corneal flap in lamellar keratoplasty or keratectomy of a precisely determined diameter regardless of corneal curvature.

It is another object of the present invention to provide an apparatus which creates a corneal flap of predetermined thickness, uniformly from center to periphery of the cornea.

It is still another object of the present invention to provide an apparatus which creates a corneal flap without an excessive increases in intraocular pressure.

It is another object of the present invention to provide an apparatus which reliably creates a corneal flap with a reduce risk of creating an amputated flap (free cap) regardless of corneal curvature.

It is another object of the present invention to provide an apparatus and method which reliably seats a corneal flap in a recessed position with reduced risk of flap distortion, flap displacement, flap amputation (free cap), flap melt, or epithelial ingrowth.

In accordance with the invention, generally stated, a device for creating a corneal flap is provided which includes an aperture located just below the plane of a cutting blade and through which the corneal plug protrudes in preparation for the lamellar cut of the microkeratome.

Another preferred embodiment features a transparent plate or applanation plate located a predetermined distance above the cutting blade and against which the corneal plug abuts or applanates. Another preferred embodiment features an adjustable mechanical stop located at or near the cutting blade plane for the prevention of a complete transection of the corneal flap.

In another preferred embodiment, the second ring (aperture) has a cutting blade (trephine) attached to its underside for creation of a circular, elliptical, ovoid, or other desired shape of keratotomy.

DESCRIPTION OF THE PREFERRED EMBODIMENT

Figure 1:
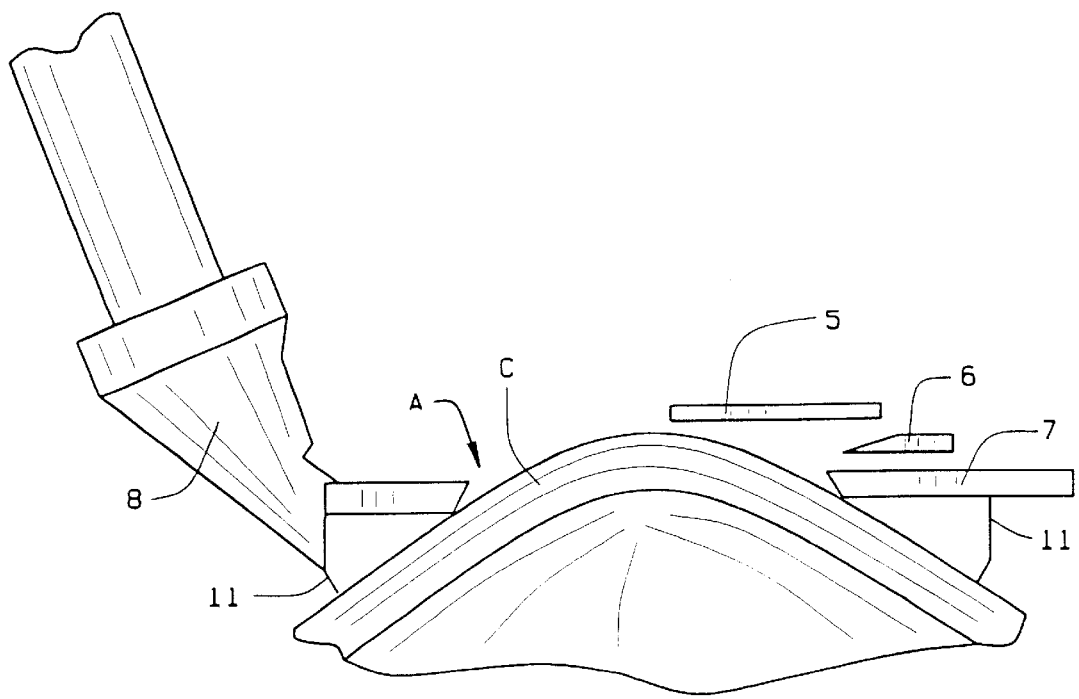
FIG. 1 is a cross-sectional view illustrating relevant features of prior art microkeratomes.

Prior art microkeratomes can generally be divided into two types, illustrated generally by FIG. 1. Ruiz-type microkeratomes feature a gear mechanism that moves the microkeratome across the cornea and an applanating surface 5 that flattens the cornea C just in front of a cutting blade 6. Hoffman-type microkeratomes feature an applanating plate 7 that flattens the entire cornea C to be fashioned into a flap before the cut begins. In both types of microkeratomes, a suction device 8 having a suction ring 11 at the limbus is used to firm the globe for the lamellar cut. The entire cornea C is exposed through an aperture A at this plane. The suction ring 11 is typically 14 mm or so in diameter and the aperture A opening is typically 12 mm or so in diameter.

Figures 2, 3:
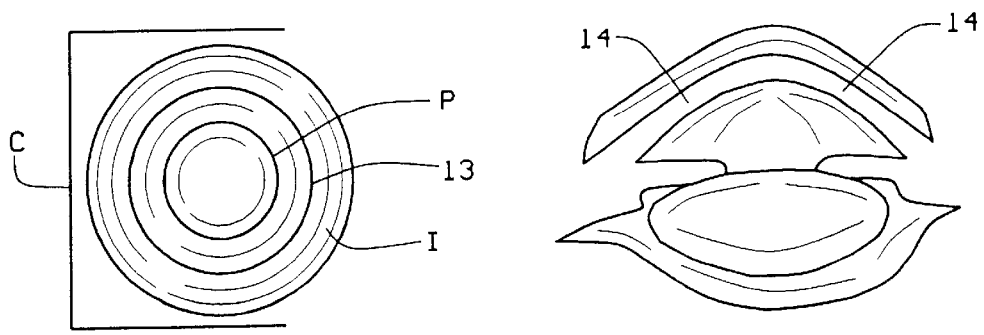
FIG. 2 is a circular cut in the cornea made by a prior art device.
FIG. 3 is a cross-sectional view of corneal circular cut shown in FIG. 2.

FIG. 2 shows a frontal view of the cornea C including the pupil P and iris I. The circular keratotomy (partial depth trephination) is shown at 13 corresponding to the desired flap size and depth. FIG. 3 shows a cross-section of the cornea C with the circular keratotomy 14.

Figure 4:
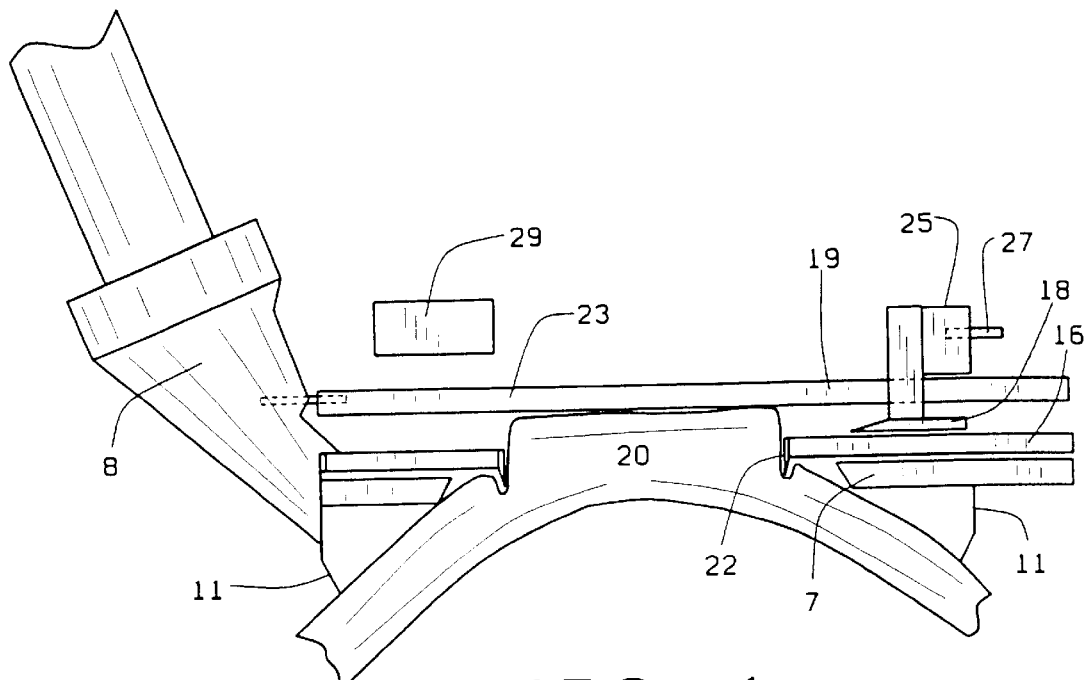
FIG. 4 is a cross-sectional view of a preferred embodiment of the present invention including a second aperture located below the plane of the cutting blade and including an applanation plate.

As illustrated in FIG. 4, the present invention adds a second aperture 16 to any type of microkeratome. The second aperture 16 is typically 10 mm or less in diameter. This second aperture is located just below the plane of the cutting blade 18. It is just slightly larger than the diameter of the trephined cornea (FIG. 2 and FIG. 3). This second aperture 16 limits the lamellar cut to incise only the corneal plug 20 protruding above the aperture 16. Optionally, this second aperture can have a cutting blade 22 of predetermined depth attached to its underside for the purpose of making the trephination (FIG. 4). As in prior art, suction 8 is applied to the suction ring 11 with first aperture A allowing prolapse of peripheral cornea below second aperture 16.

Furthermore, the present invention features a transparent applanating plate 19, which optionally is removable. This plate 19 is positioned a predetermined distance above the cutting blade 18. This distance determines the flap thickness. It confirms that the protruding corneal plug 20 is sufficiently exposed to allow a corneal flap of predetermined thickness. Cutting blade 18 is attached to a drive mechanism 23 by collar assembly 25 through a connector 27.

Figure 5:
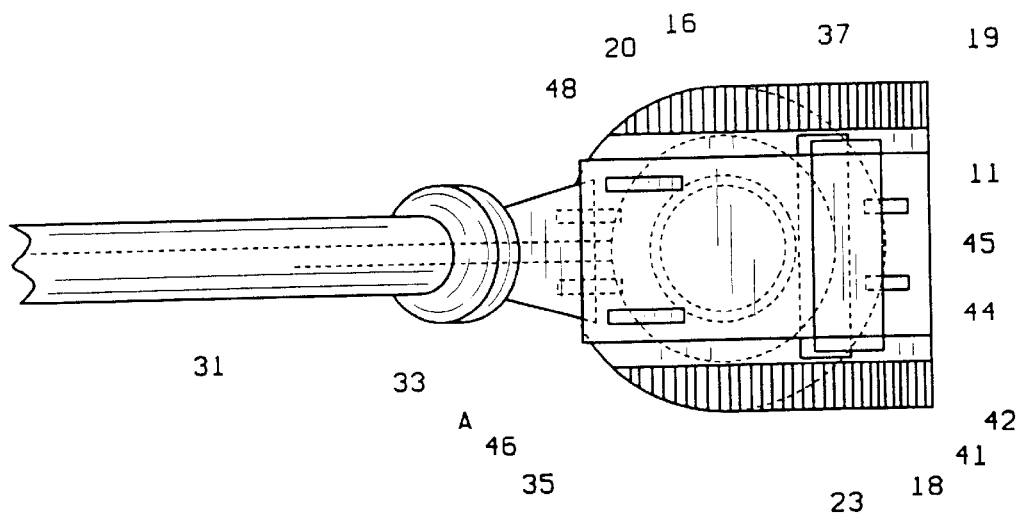
FIG. 5 is a top plan view of another preferred embodiment the present invention including an adjustable stop.

An adjustable mechanical stop 29 can be used to prevent a free cap and to predetermine the flap hinge width, as shown in FIG. 5. The stop 29 can be placed at or near the plane of the cutting blade 18 or the drive mechanism 23.

In FIG. 5, a top view of the present invention shows a suction-handle 31 through which suction pressure is applied to the suction ring 11 via channels 33. In this embodiment, gear tracks 35 and 37 provide traction for a transverse drive mechanism. 23. Other drive mechanisms are available, such as a cable drive, and are contemplated by the present invention. The transparent applanation plate 19 is used to confirm that the corneal plug 20 is in uniform contact with the underside of the applanating plate, thus confirming that the lamellar flap will be the desired thickness. The corneal plug 20 prolapses through the second aperture 16, which is typically no more than 10 mm or so in diameter, optionally less. The first aperture A is typically 12 mm or so in diameter. The cutting blade 18 is positioned a predetermined distance below the transparent applanation plate 19 and just above the plane of the second aperture 16. The cutting blade 18 is attached to the drive mechanism 23 by a collar 41 whose connecting member 42 is connected via studs 44 to a drive motor 45. In this embodiment, a movable stop 46 on track 48 is placed at the plane of the cutting blade 18, its position adjusted so as to ensure a hinge of tissue, thus preventing a "free" cap.

In practice, the present invention is used by the surgeon in the following way. The surgeon decides what flap diameter and flap thickness he desires. The surgeon places the present invention with the appropriately sized second aperture 16 slightly larger than the desired flap diameter, centering it and, preferably, applying mild-moderate suction pressure (e.g., 30–50 mm Hg or so). A circular trephination of the desired flap diameter and flap thickness is performed, preferably with the apparatus disclosed in my copending application Ser. No. 09/188,160 which is incorporated by reference. The corneal plug 20 protrudes through the second aperture 16, making contact with a transparent plate 19 (applanation plate) positioned at a height above the second aperture 16 which is identical to the desired flap thickness. The surgeon inspects the applanation to confirm that there is uniform contact with the surface of the corneal plug 20. The surgeon then adjusts the mechanical stop, placing it at a position sufficient to create a hinge of predetermined width for the flap. The surgeon then engages the microkeratome device to incise the flap.

What is claimed is:

1. A microkeratome having a first aperture having suction means and a cutting means for use in the creation of a lamellar corneal flap comprising:

a second aperture of predetermined size slightly larger than the desired corneal flap, said second aperture located just below a plane of the cutting means, said second aperture accommodating a cutting means for trephining; and a transparent applanation plate positioned above the plane of said cutting means.

2. The microkeratone of claim 1 wherein the second aperture further accommodates a trephining blade.

3. The microkeratome of claim 1 and further comprising an adjustable stop to prevent a complete transection of the corneal flap.

4. The microkeratome of claim 1 wherein the second aperture further accommodates a second cutting blade.

5. The microkeratome of claim 1 and further incorporating a suction apparatus.

6. A microkeratome having a first aperture and a cutting blade for use in the creation of a lamellar corneal flap comprising:

a second aperture of predetermined size slightly larger than the desired size of the lamellar corneal flap positioned below the plane of the cutting blade;

a transparent applanation plate positioned at a predetermined distance above the plane of the cutting blade; and a suction device.

7. The microkeratome of claim 6 and further comprising a stop to prevent a complete transection of the corneal flap.

8. The microkeratome of claim 7 wherein the stop is an adjustable stop.

9. A microkeratome apparatus having a first aperture suction means and first cutting blade for use in the creation of a lamellar corneal flap of a desired size comprising:
- a second aperture of predetermined size, said predetermined size being slightly larger than the desired size of the lamellar corneal flap, said second aperture positioned just below a plane of the first cutting blade, and accommodating a second cutting blade;
- a transparent applanation plate positioned at a predetermined distance above the plane of the first cutting blade;
- an adjustable stop to prevent a complete transection of the corneal flap; and
- a drive mechanism connected to at least one of said first or second cutting blades.

10. The microkeratome of claim 8 wherein the stop is an adjustable mechanical stop.

11. The microkeratome of claim 9 wherein the second aperture further accommodates a second cutting blade.

12. The microkeratome of claim 9 and further including a suction apparatus.

13. The microkeratome of claim 9 and further comprising said drive mechanism operatively connected to at least one of said first or second cutting blades.

* * * * *